United States Patent [19]

Ferrini et al.

[11] 4,308,277
[45] Dec. 29, 1981

[54] 2,4,5-TRISUBSTITUTED IMIDAZOLINES AND PHARMACEUTICAL COMPOSITIONS CONTAINING SAME

[75] Inventors: Pier G. Ferrini, Binningen; Richard Göschke, Bottmingen, both of Switzerland

[73] Assignee: Ciba-Geigy Corporation, Ardsley, N.Y.

[21] Appl. No.: 61,792

[22] Filed: Jul. 30, 1979

[30] Foreign Application Priority Data

Aug. 10, 1978 [CH] Switzerland .................. 8526/78

[51] Int. Cl.³ ............... C07D 233/30; C07D 401/04; A61K 31/415
[52] U.S. Cl. ............................... 424/273 R; 424/263; 546/278; 548/348; 548/351
[58] Field of Search ................. 548/351, 348; 424/273 R, 263; 546/278

[56] References Cited

U.S. PATENT DOCUMENTS

| | | | |
|---|---|---|---|
| 2,981,739 | 4/1961 | Bimber | 548/351 |
| 4,182,769 | 1/1980 | Cherkofsky et al. | 424/273 R |
| 4,190,666 | 2/1980 | Cherkofsky et al. | 424/274 |

FOREIGN PATENT DOCUMENTS

| | | | |
|---|---|---|---|
| 2805166 | 8/1978 | Fed. Rep. of Germany | 548/342 |
| 1516908 | 7/1978 | United Kingdom | 548/342 |

*Primary Examiner*—Alan L. Rotman
*Attorney, Agent, or Firm*—Prabodh I. Almaula

[57] ABSTRACT

Compounds of the formula

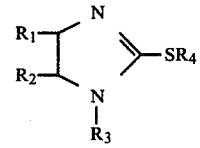
(I)

in which $R_1$ and $R_2$ independently of one another are substituted or unsubstituted aryl or hetero-aryl groups, $R_3$ is hydrogen or lower alkyl and $R_4$ is a substituted or unsubstituted aliphatic hydrocarbon radical, and their pharmaceutically usable salts. These compounds possess immunoregulatory, antithrombotic and antiinflammatory properties and can be used as active ingredients in medicaments. They are prepared, for example, by reacting compounds of the formulae

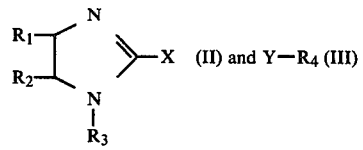

in which one of the radicals X and Y is mercapto, which can be in the form of a salt, and the other is a radical replaceable by etherified mercapto, with one another.

15 Claims, No Drawings

2,4,5-TRISUBSTITUTED IMIDAZOLINES AND PHARMACEUTICAL COMPOSITIONS CONTAINING SAME

The present invention relates to novel thio-substituted diazacycloalkenes, especially compounds of the formula

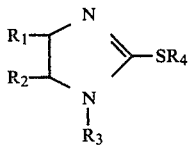 (I)

in which $R_1$ and $R_2$ independently of one another are substituted or unsubstituted aryl or hetero-aryl groups, $R_3$ is hydrogen or lower alkyl and $R_4$ is a substituted or unsubstituted aliphatic hydrocarbon radical, and their salts, processes for their preparation, pharmaceutical preparations which contain compounds of the formula I or pharmaceutically usable salts thereof and the use of the compounds defined above.

In this specification "lower" organic radicals and compounds are to be understood as meaning those which contain not more than 7 and in particular not more than 4 carbon atoms.

Aryl groups are, for example, phenyl groups. Hetero-aryl groups are, for example, thienyl or pyridyl groups, such as 2- or 3-thienyl or 2-, 3- or 4-pyridyl. Examples of substituents of these groups are lower alkyl, lower alkoxy, halogen, substituted or unsubstituted amino, trifluoromethyl and/or nitro. Thienyl, such as 2-thienyl, and pyridyl groups $R_1$ and $R_2$ are preferably unsubstituted.

Substituted amino groups are monosubstituted or preferably disubstituted amino groups, possible substituents being, for example, lower alkyl or alkylene having 4 to 7 ring members, which can be interrupted by a nitrogen, oxygen or sulfur atom, such as lower alkylamino, di-lower alkylamino or lower alkyleneamino or 3-aza-, 3-oxa- or 3-thia-lower alkyleneamino, having 5 or 6 ring members in each case. In addition to methylamino and ethylamino, example are, in particular, dimethylamino, diethylamino, pyrrolidino, piperidino, morpholino, thiomorpholino, piperazino and N'-lower alkyl-piperazino, for example N'-methylpiperazino.

Aliphatic hydrocarbon radicals are, for example, lower alkyl radicals, which can be unsaturated, such as lower alkyl, lower alkenyl or lower alkynyl.

Substituents of aliphatic hydrocarbon radicals are, for example, substituted or unsubstituted aryl, such as phenyl, radicals, free or esterified carboxyl, such as carboxyl or lower alkoxycarbonyl, or hydroxyl, lower alkoxy, lower alkylthio or substituted or unsubstituted aryloxy, such as phenoxy, or arylthio, such as phenylthio, groups which are bonded in a position higher than the α-position.

Aliphatic hydrocarbon radicals are preferably lower alkyl, lower alkenyl or lower alkynyl rdicals which are unsubstituted or substituted as indicated, for example lower alkyl, lower alkenyl, substituted or unsubstituted phenyl-lower alkyl, carboxy-lower alkyl or lower alkoxycarbonyl-lower alkyl, or lower alkyl radicals substituted in a position higher than the α-position by halogen, in particular fluorine, hydroxyl, lower alkoxy, or lower alkylthio or by substituted or unsubstituted phenoxy or phenylthio, it being possible for several substituents, in particular several halogen atoms, to be present.

Lower alkyl which can be unsaturated and can be substituted by phenyl is, for example, lower alkyl, such as $C_1$–$C_4$-alkyl, phenyl-lower alkyl, such as 1- or 2-phenyl-$C_1$–$C_4$-alkyl, which is unsubstituted or substituted as indicated, for example benzyl or 2-phenylethyl, lower alkenyl, such as $C_2$–$C_4$-alkenyl, for example vinyl, allyl or methallyl, phenyl-lower alkenyl, such as 2-phenyl-$C_2$–$C_4$-alkenyl, which is unsubstituted or substituted as indicated, for example styryl, lower alkynyl, such as $C_2$–$C_4$-alkynyl, for example ethynyl or propargyl, or phenyl-lower alkynyl, such as phenyl-$C_2$–$C_4$-alkynyl, which is unsubstituted or substituted as indicated, for example 2-phenylethynyl.

Hydroxy-lower alkyl is, for example, mono- or di-hydroxy-lower alkyl, such as mono- or di-hydroxy-$C_2$–$C_4$-alkyl, for example 2-hydroxyethyl, 2- or 3-hydroxypropyl or 2,3-dihydroxypropyl.

Halogeno-lower alkyl is, for example, mono-, di- or tri-halogeno-lower alkyl, such as 2,2,2-trichloroethyl or 2,2,2-trifluoroethyl.

Lower alkoxy-lower alkyl is, for example, $C_1$–$C_4$-alkoxy-lower alkyl, such as $C_{1-C4}$-alkoxy-$C_1$–$C_4$-alkyl, for example 2-methoxyethyl, 2-ethoxyethyl or 2- or 3-methoxypropyl.

Lower alkylthio-lower alkyl is, for example, $C_1$–$C_4$-alkylthio-$C_1$–$C_4$-alkyl, such as 2-methoxylthioethyl.

Phenoxy-lower alkyl is, for example, phenoxy-$C_1$–$C_4$-alkyl which is unsubstituted or substituted as indicated, such as 2-phenoxyethyl, and phenylthio-lower alkyl is likewise, for example, phenylthio-$C_1$–$C_4$-alkyl which is unsubstituted or substituted as indicated, such as 2-phenylthioethyl.

Lower alkyl is, for example, $C_1$–$C_4$-alkyl, such as methyl, ethyl, propyl, isopropyl or n-, iso-, sec.- or tert.-butyl or, less preferentially, one of the isomeric pentyl, hexyl or heptyl groups.

Lower alkoxy is, for example, $C_1$–$C_4$-alkoxy, such as methoxy, ethoxy, propoxy, isopropoxy or n-, sec.-, iso- or tert.-butoxy or, less preferentially, one of the isomeric pentyloxy, hexyloxy, heptyloxy groups.

Lower alkylthio is, for example, $C_1$–$C_4$-alkylthio, such as methylthio, ethylthio, propylthio, isopropylthio or butylthio or, less preferentially, pentylthio, hexylthio or heptylthio.

Lower alkenyl is, for example, $C_2$–$C_4$-alkenyl, such as vinyl, allyl or methallyl, whilst lower alkynyl is, for example, $C_2$–$C_4$-alkynyl, in particular ethynyl or propargyl.

Halogen is preferably halogen with an atomic number of not more than 35, i.e. fluorine, chlorine or bromine.

Salts of compounds of the formula I are, for example, acid addition salts, in particular pharmaceutically usable acid addition salts with strong acids, such as a mineral acid, for example salts with hydrogen halide acids, in particular hydrochloric acid or hydrobromic acid, i.e. hydrohalides, in particular hydrochlorides and hydrobromides, or sulfuric acid salts, i.e. bisulfates and sulfates.

Because of the asymmetric C atoms in the 4- and 5-position of the imidazole ring, the compounds of the formula I are dissymmetrical and form stereoisomers. Accordingly, they arise in at least four stereoisomeric forms, i.e. two cis forms which are enantiomeric to one another and have either the meso- or (+)- or (−)-erythro-configuration, and two trans forms which are enantiomeric to one another and have either the D,L- or (+)-threo- or (−)-threo-configuration, each cis form being diastereomeric to each trans form. In the case of compounds of the formula I in which $R_1$, $R_2$, $R_3$ and/or $R_4$ contain asymmetric carbon atoms, further possibilities for isomerism must be taken into account.

Accordingly, the compounds of the formula I can be in the form of an individual stereoisomer, for example enantiomer, or in the form of mixtures of at least two stereoisomers, for example in the form of a mixture of diastereomers, or mixtures of enantiomers, such as racemates.

The compounds of the formula I have valuable pharmacological properties. In particular they have a pronounced anti-inflammatory, antithrombotic, and/or antinociceptive activity. Thus, when employed prophylactically, they inhibit kaolin paw oedema in normal rats in two administrations of about 100 to about 300 mg/kg perorally and, when employed curatively, inhibit kaolin paw oedema in adjuvant arthritis rats on four administrations of about 30 to 100 mg/kg perorally. Furthermore, they inhibit the phenyl-p-benzoquinone-induced writhing syndrome in mice and likewise inhibit the writhing syndrome induced by the intravenous injection of 0.2 ml of 3% acetic acid in rats, when employed prophylactically in doses of, in each case, about 30 to about 100 mg/kg administered perorally. Furthermore, in experimental pulmonary embolism in rabbits, they are effective in a dosage range of about 3 to about 30 mg/kg administered perorally, and in vitro, in a concentration range of about 100 to about 200 mg/l, inhibit the prostaglandin synthesis from arachidonic acid by spermatocystic enzymes in cattle.

The compounds of the formula I are therefore outstandingly suitable as inflammatoric agents for the treatment of inflammatory diseases, in particular chronic inflammation of the rheumatic type, such as chronic arthritis, and/or as analgesics.

The invention relates especially to compounds of the formula I in which $R_1$ and $R_2$ independently of one another are substituted or unsubstituted phenyl, thienyl or pyridyl groups, $R_3$ is hydrogen or lower alkyl and $R_4$ is an aliphatic hydrocarbon radical having not more than 7 carbon atoms which is unsubstituted or monosubstituted by carboxyl or lower alkoxycarbonyl, for example in the α-position, by substituted or unsubstituted phenyl or, in a position higher than the α-position, by hydroxyl, lower alkoxy, such as methoxy or ethoxy, lower alkylthio, such as methylthio, or a substituted or unsubstituted phenoxy or phenylthio group, or monosubstituted or polysubstituted by halogen, it being possible for phenyl, phenoxy, phenylthio and pyridyl groups to be substituted by lower alkyl, such as methyl, lower alkoxy, such as methoxy or ethoxy, halogen with an atomic number of not more than 35, such as fluorine or chlorine, trifluoromethyl, nitro and/or amino which can contain, as substituents, lower alkyl, such as methyl, or 4-membered to 7-membered alkylene, such as tetramethylene or pentamethylene, which can be interrupted by nitrogen, oxygen or sulfur, and their salts.

The invention relates in particular to compounds of the formula I in which $R_1$ and $R_2$ independently of one another are substituted or unsubstituted phenyl, thienyl or pyridyl, $R_3$ is hydrogen or, less preferentially, lower alkyl, such as methyl, and $R_4$ is lower alkyl which is unsubstituted or monosubstituted by phenyl or, in a position higher than the α-position, by hydroxyl, lower alkoxy, lower alkylthio, phenoxy or phenylthio, or monosubstituted or polysubstituted by halogen with an atomic number of not more than 35, or is a lower alkenyl or lower alkynyl radical which is unsubstituted or substituted by phenyl, it being possible for phenyl, phenoxy and phenylthio groups to be substituted by lower alkyl, such as methyl, lower alkoxy, such as methoxy or ethoxy, halogen with an atomic number of not more than 35, such as chlorine, nitro, amino or N,N-di-lower alkylamino, such as dimethylamino, and for pyridyl groups to be substituted by lower alkyl, such as methyl, or lower alkoxy, such as methoxy or ethoxy, and their salts.

The invention preferentially relates to compounds of the formula I in which $R_1$ and $R_2$ independently of one another are phenyl which is unsubstituted or substituted by lower alkyl having not more than 4 C atoms, such as methyl, lower alkoxy having not more than 4 C atoms, such as methoxy, or halogen with an atomic number of not more than 35, such as chlorine, or, less preferentially, are unsubstituted pyridyl, such as 2-, 3- or 4-pyridyl, $R_3$ is hydrogen and $R_4$ is lower alkyl having not more than 4 C atoms, such as methyl, ethyl or propyl, or ω,ω,ω-trihalogeno-lower alkyl having not more than 4 C atoms, such as 2,2,2-trihalogenoethyl, for example 2,2,2-trifluoroethyl, and their salts, in particular their pharmaceutically usable acid addition salts.

The invention relates specifically to the compounds of the formula I named in the examples.

The novel compounds can be prepared by processes known per se, for example by reacting compounds of the formulae

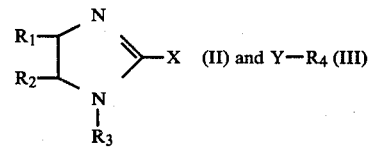

in which one of the radicals X and Y is mercapto, which can be in the form of a salt, and the other is a radical replaceable by etherified mercapto, with one another or reacting a compound of the formula II in which X is a mrecapto group with a lower alkene, which can be substituted as indicated, and, if desired, converting the resulting compound into another compound of the formula I, separating a mixture of stereoisomers, which may be obtained, into the components and/or converting a resulting free compound into a salt or converting a resulting salt into the free compound or into another salt.

Mercapto in the form of a salt is, for example, mercapto in the form of an alkali metal salt, for example in the form of the sodium or potassium salt.

Radicals X and Y replaceable by etherified mercapto are, for example, halogen atoms, for example chlorine, bromine or iodine, and radicals X replaceable by the group —$SR_4$ are also sulfonyl groups, in particular sulfonyl groups derived from organic sulfonic acids, for example methanesulfonyl, ethanesulfonyl, benzenesulfonyl, p-bromobenzenesulfonyl or p-toluenesulfonyl. Radicals Y replaceable by 1-$R_3$-4-$R_1$-5-$R_2$-4-imidazolin-2-yl-thio are, furthermore, reactively esterified hydroxyl groups other than halogen, such as hydroxyl groups esterified with sulfuric acid or with an organic sulfonic acid, for example with methanesulfonic acid, ethanesulfonic acid, benzenesulfonic acid, p-bromobenzenesulfonic acid or p-toluenesulfonic acid.

The reaction can be carried out in a conventional manner, especially in the manner known from the literature for analogous reactions, if necessary in the presence off a catalytic agent, for example in the presence of acid agents, such as mineral acids or Lewis acids, for example boron trifluoride, in the case of the reaction of mercapto compounds of the formula II with alkenes or phenylalkenes, and preferably in a solvent, for example in ether, tetrahydrofuran or dioxan in the case of the reaction of mercapto compounds of the formula II with alkenes or phenylalkenes, or in an alcohol, for example in methanol, ethanol, ethylene glycol or ethylene glycol monomethyl ether, in the case of the reaction of mercaptans with halides, the reaction in each case advantageously being carried out under an inert gas atmosphere, for example under nitrogen, and if necessary at elevated temperature, for example at the boil.

A preferred embodiment of the above process comprises, for example, reacting a 2-mercapto-4-imidazoline derivative of the formula II, which can be in the form of one of the said salts, in a lower alkanol, for example in methanol or ethanol, with a hydrochloric acid ester, hydrobromic acid ester, hydriodic acid ester or sulfuric acid ester or the formula III.

The starting materials are known or can be prepared in a manner known per se.

Compounds of the formula II in which X is mercapto can, for example, be prepared by reacting a compound of the formula $R_1$—CH(NH$_2$)—CH(NHR$_3$)—R$_2$ (IIa) with carbon disulfide in a conventional manner. Compounds of the formula IIa in which R$_3$ is hydrogen can be obtained, for example, by converting a corresponding 1,2-diketone of the formula $R_1$—C(=O)—C(=O)—R$_2$ (IIb) to the oxime and reducing the dioxime of the formula $R_1$—C(=NOH)—C(=NOH)—R$_2$ (IIc) in a conventional manner. If the reducing agent used is sodium and an alcohol, the meso-diamine is preferentially obtained, whilst in the main the D,L-diamine is obtained by catalytic hydrogenation. Compounds of the formula IIa in which R$_3$ differs from hydrogen are prepared, for example, by first reacting an α-halogenoketone, for example of the formula R$_2$—CHBr—C(=O)—R$_1$ (IId), with an amine of the formula R$_3$NH$_2$, converting the reaction product, for example of the formula R$_2$—CH(NHR$_3$)—C(=O)—R$_1$ (IIe), to the oxime and reducing the resulting amino-oxime, for example of the formula R$_2$—CH(NHR$_3$)—C(=NOH)—R$_2$ (IIf), in a conventional manner, for example as indicated above.

Compounds of the formula II in which X is halogen can be obtained, for example, by halogenating a corresponding 4-R$_1$-5-R$_1$-imidazolindin-2-one, obtainable, for example, from a urea and a 1-R$_1$-2-R$_2$-1,2-dibromoethane or from a diamine of the formula IIa by reaction with a carbonic acid diester or carbonic acid ester-chloride, in the 2-position in a conventional manner, for example with phosphorus tribromide, phosphorus pentachloride or the like.

Compounds of the formula II in which X is sulfonyl can be prepared, for example, by reacting a compound of the formula

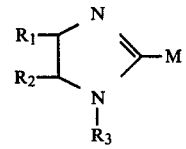 (IIg)

in which M is a metal radical, such as an alkali metal atom, for example lithium, or a halogeno-alkaline earth metal radical, for example of the formula —MgBr, in a conventional manner with a corresponding sulfonyl halide, for example of the formula X—Cl (IIh). The compounds of the formula IIg which are to be used as starting materials for this reaction are advantageously prepared in situ by conventional reaction of a corresponding 4-R$_1$-5-R$_2$-4-imidazoline compound, which is unsubstituted in the 2-position, with a metal-hydrocarbon compound, for example with butyl-lithium or butyl-magnesium bromide, and are reacted without isolation. Compounds of the formula II in which X is a sulfonyl group R$_4'$—SO$_2$— which differs from sulfonyl R$_4$—SO$_2$—, for example is substituted or unsubstituted benzenesulfonyl, such as p-toluenesulfonyl, can furthermore be prepared by oxidising the R$_4'$—S group in a compound of the formula

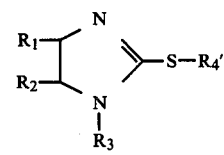 (IIi)

in a conventional manner, for example by reaction with a hydroperoxy compound, for example with m-chloroperbenzoic acid or hydrogen peroxide in acetic acid, to —SO$_2$R$_4'$. The compounds of the formula (IIi) which are to be used as starting materials for this reaction can be prepared, for example, by reacting a compound of the formula

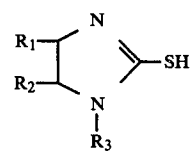 (II')

or preferably an alkali metal salt, such as the sodium salt, thereof, with a compound of the formula R$_4'$Hal, in which Hal is halogen, such as chlorine, bromine or iodine, and, if desired, introducing a substituent into the 1-position of resulting compounds of the formula II in which R$_3$ is hydrogen, by reaction with a lower alkyl halide of the formula R$_3$—Hal.

The novel compounds can also be prepared by cyclising a compound of the formula

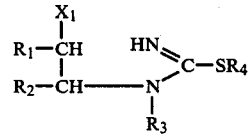 (IV)

in which X$_1$ is a radical replaceable by imino, or a salt thereof, and, if desired, converting the resulting compound into another compound of the formula I, separating a mixture of stereoisomers, which may be obtained, into the components and/or converting a resulting free compound into a salt or converting a resulting salt into the free compound or into another salt.

Radicals $X_1$ replaceable by imino are, for example, free or esterified hydroxyl groups or amino groups. Esterified hydroxyl groups are, for example, reactively esterified hydroxyl groups, such as halogen, for example chlorine or bromine, or sulfonyloxy groups, for example methanesulfonyloxy, benzenesulfonyloxy or p-toluenesulfonyloxy.

Salts of compounds of the formula IV are, for example, the acid addition salts thereof with mineral acids, such as the hydrohalides or sulfates thereof.

The cyclisation is effected in a conventional manner, for example in the presence of a condensing agent, such as an inorganic base, such as an alkali metal hydroxide, carbonate or bicarbonate, for example sodium hydroxide or potassium hydroxide, potassium carbonate or sodium bicarbonate, or a tertiary organic nitrogen base, for example triethylamine or pyridine, preferably in a solvent which is inert under the reaction conditions and if necessary at elevated or lowered temperature, for example at about 0° to about 100° C.

The starting materials of the formula IV are advantageously prepared in situ. Thus, for example, a diamine of the formula $R_1$—CH($NH_2$)—CH($NR_3$)—$R_2$ (IIa) or a corresponding 1-$R_1$-2-$R_2$-ethylene oxide can be reacted with a $R_4$-isothiourea or the corresponding isothiuronium salt, for example a corresponding hydrohalide, to give a compound of the formula III in which $X_1$ is amino. The diamine of the formula IIa can be obtained, for example, by reacting a bromoketone of the formula $R_1$—C(=O)—CHBr—$R_2$ (IId) with a $R_3$-amine, converting the reaction product of the formula $R_1$—C(=O)—CH($NHR_3$)—$R_2$ (IIe) or a diketone of the formula $R_1$—C(=O)—C(=O)—$R_2$ (IIb) to the oxime and reducing the oxime of the formula $R_1$—C(=NOH)—CH($NHR_3$)—$R_2$ (IIf) or $R_1$—C(=NOH)—C(=NOH)—$R_2$, which is thus obtainable, in a conventional manner. Analogously, a dihalide of the formula $R_1$—$CHX_1$—$CHX_1$—$R_2$ (IVa), in which $X_1$ is halogen, for example bromine, can be reacted with a $R_4$-isothiourea or the corresponding isothiuronium salt. Dihalides, in particular dichlorides, of the formula IIIa are accessible, for example, by halogenating, for example chlorinating, a corresponding olefin of the formula $R_1$—CH=CH—$R_2$ (IVb) in a conventional manner at the double bond.

In order to prepare compounds of the formula IV in which $X_1$ is hydroxyl, a corresponding α-halogenoketone, for example of the formula $R_1$—C(=O)—CHBr—$R_2$ (IId), is advantageously used as the starting material and this is reacted with a S—$R_4$-thiourea or the corresponding isothiuronium salt, and the carbonyl group in the condensation product of the formula

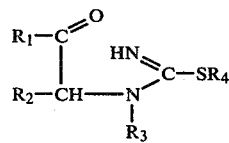

(IVc)

is reduced to hydroxymethylene in a conventional manner, for example by means of sodium borohydride or sodium cyanoborohydride.

The compounds of the formula I can also be prepared by converting $X_2$ in a compound of the formula

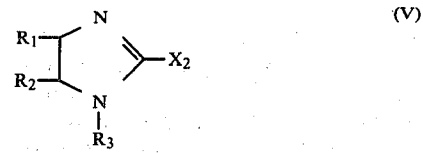

(V)

in which $X_2$ is a radical convertible to a radical $R_4S$—, into the desired radical $R_4S$—and, if desired, converting the resulting compound into another compound of the formula I, separating a mixture of stereoisomers, which may be obtained, into the components and/or converting a resulting free compound into a salt or converting a resulting salt into the free compound or into another salt.

Groups $X_2$ which are convertible to radicals of the formula $R_4S$—are, for example, those of the formula $R_4''$—S(O)$_n$—, in which n is 0, 1 or 2 and $R_4''$ is a radical convertible to $R_4$ or, if n is 1 or 2, is a radical $R_4$. Groups convertible to radicals $R_4$ are, for example, radicals $R_4$ which are substituted in the aliphatic moiety by free or esterified carboxyl, or carboxyl in the form of an anhydride, epoxy, functionally modified hydroxyl or oxo and/or ammonium or sulfonium groups. Esterified carboxyl is, for example, carboxyl esterified with an aliphatic, araliphatic or aromatic alcohol, such as lower alkoxycarbonyl or substituted or unsubstituted phenoxycarbonyl. Carboxyl in the form of an anhydride is, for example, carboxyl converted to an anhydride with a hydrogen halide acid, such as halogenocarbonyl. Functionally modified hydroxyl is, for example, esterified hydroxyl, such as hydroxyl esterified with a carboxylic acid or organic sulfonic acid, such as lower alkanoyloxy, for example acetoxy, or substituted or unsubstituted benzoyloxy, or alkanesulfonyloxy or substituted or unsubstituted benzenesulfonyloxy, for example methanesulfonyloxy, ethanesulfonyloxy, benzenesulfonyloxy, p-toluenesulfonyloxy or mesitylenesulfonyloxy. Functionally modified oxo is, for example, hydrazono, which can be substituted in the β-position by 2-sulfonyl, for example p-toluenesulfonyl or mesitylenesulfonyl. Ammonium groups are, for example, disubstituted or trisubstituted ammonium groups, for example di-or tri-lower alkyl-ammonium groups or di-lower alkylamine oxide groupings. Sulfonium groups are, for example, disubstituted sulfonium groups, such as di-lower alkylsulfonium groups or lower alkane-sulfinyl or-sulfonyl or substituted or unsubstituted benzenesulfinyl or-sulfonyl, such as methane-, ethane-, benzene-, p-toluene- or mesitylene-sulfinyl or the corresponding sulfonyl groups.

The conversion of groups $X_2$ into groups of the formula $R_4S$— is effected in a conventional manner, for example by reduction, solvolysis, replacement and/or elimination methods.

By means of reduction it is possible, for example, in a group $X_2$ of the formula $R_4''$—S(O)$_n$—, in which n is 0, 1 or 2 and $R_4''$ is a radical $R_4$ which is substituted by free or esterified carboxyl, or carboxyl in the form of an anhydride, hydrazono, which can be substituted in the aliphatic moiety, oxo and/or esterified hydroxyl, or, if n is 1 or 2, is an unsubstituted radical $R_4$, to convert sulfinyl or sulfonyl to thio, to convert free or esterified carboxyl, or carboxyl in the form of an anhydride, to unsubstituted or C-substituted hydroxymethyl, and/or to convert oxo, epoxy or hydroxyl esterified with a carboxylic acid to hydroxyl and/or to replace oxo, substituted or unsubstituted hydrazono or hydroxyl esterified with an organic sulfonic acid by hydrogen.

The reduction can be effected by reaction with a conventional reducing agent, for example with a light metal hydride or di-(light metal) hydride, such as a borane, for example diborane or the borane-tetrahydrofuran complex, an alkali metal borohydride, for example sodium borohydride, lithium borohydride or sodium cyanoborohydride, an aluminium hydride, for example triisobutyl aluminium hydride, or an alkali metal aluminium hydride, for example lithium aluminium hydride. Thus, using lithium aluminium hydride it is possible, for example, to reduce oxo, epoxy or hydroxyl esterified with a carboxylic acid to hydroxyl, to reduce free or esterified carboxyl, or carboxyl in the form of an anhydride, to hydroxymethyl and to reduce sulfinyl or sulfonyl to thio and to replace terminal sulfonyloxy by hydrogen. The reaction is carried out in a conventional manner, for example in a solvent which is inert towards the reactants, if necessary at elevated or lowered temperature, for example at about 0° to 100° C. The reduction of oxo to hydroxyl, of carboxyl in the form of an anhydride to hydroxymethyl and of sulfinyl to thio can also be effected by reaction with sodium borohydride or sodium cyanoborohydride, advantageously in an alcohol, such as a lower alkanol, for example in ethanol, or in a carboxylic acid amide, such as N-methylpyrrolidone, N,N-dimethylformamide or N-methylacetamide, or in a mixture thereof, preferably an aqueous mixture thereof. However, it is also possible, for example, to use diborane for the reduction of oxo to hydroxyl, of carboxyl to hydroxymethyl and of sulfinyl or sulfonyl to thio, and also to use triisobutyl aluminium hydride to replace a terminal sulfonyloxy group by hydrogen. The reduction of oxo to hydroxyl and of free or esterified carboxyl, or carboxyl in the form of an anhydride, to C-substituted hydroxymethyl can be effected by reaction with an aliphatic, araliphatic or heteroaliphatic alkali metal or alkaline earth metal compound, such as a corresponding lithium or halogenomagnesium compound, advantageously in an ether-like solvent, for example in diethyl ether, tetrahydrofuran or dioxan, if necessary with cooling or warming, for example at about 0° to 100° C. By this means oxo is reduced to secondary hydroxyl, and free or esterified carboxyl, or carboxyl in the form of an anhydride, is reduced to C-substituted hydroxymethyl. The above reductions are advantageously carried out under an inert gas, such as nitrogen, and if necessary in a closed vessel.

The replacement of oxo by hydrogen by means of reduction can be effected, for example, by means of nascent hydrogen, which advantageously is produced in situ by the action of proton donors on base metals, for example of proton acids, such as hydrochloric acid or acetic acid, on iron, zinc or aluminium, or of water or alcohols, such as ethanol, or mixtures thereof, on an amalgam of aluminium or zinc, of water on sodium amalgam or of alcohols, such as methanol, on sodium. The replacement of substituted or unsubstituted hydrazono by hydrogen by means of reduction is preferably effected by disproportionation, for example by heating with a metal base, such as an alkali metal hydroxide or alkali metal alcoholate, for example with potassium hydroxide or sodium methanolate, advantageously in a high-boiling solvent, such as a high-boiling alcohol, for example ethylene glycol, ethylene glycol monomethyl ether, diethylene glycol or diethylene glycol monomethyl ether, to about 100° to 250° C., advantageously under an inert gas.

By means of solvolysis, such as hydrolysis or alcoholysis in the presence of an acid or basic agent, it is possible, for example, to convert hydroxyl esterified with a carboxylic acid to hydroxyl. The acid agents used are preferably proton acids, such as mineral acids, for example hydrochloric acid or sulfuric acid. Suitable basic agents are, for example, metal bases, and in the case of hydrolysis preferably alkali metal hydroxides, for example sodium hydroxide or potassium hydroxide, if desired in aqueous methanol or ethanol, or in the case of alcoholysis preferably alkali metal alcoholates, in particular those of low-boiling alcohols, such as sodium methanolate.

By means of replacement it is possible, for example, to convert carboxyl which can be in the form of an acid anhydride to trihalogenomethyl or to replace oxo by two halogen atoms. For this purpose, the reaction is carried out with conventional halogenating agents, for example with phosphorus pentachloride or with sulfur tetrafluoride. For the conversion of carboxyl to trifluoromethyl it is more economical first to convert the carboxyl group by reaction with a secondary aminosulfur trifluoride, for example diethylaminosulfur trifluoride, to fluorocarbonyl and then to perfluorinate the latter with sulfur tetrafluoride. Furthermore, a carboxyl group can be replaced by hydrogen, preferably by decarboxylation, preferably by heating at about 100° to 250° C., if necessary in the presence of copper compounds and/or in a high-boiling solvent, such as diphenyl ether, dimethylformamide or diethylene glycol mono- or di-methyl ether.

By means of elimination, for example, β-sulfonylhydrazono groups and also ammonium or sulfonium groups together with a vicinal hydrogen atom can be detached, with the formation of a double bond. The elimination is effected in a conventional manner, by treatment with a base and/or heating to about 100° to 250° C. When the starting groups are β-sulfonylhydrazono groups, the bases used are, for example, strong metal bases, such as lithium-hydrocarbon compounds, such as butyl-lithium, and when the starting groups are di- or tri-lower alkylammonium or di-lower alkylsulfonium groups, the bases used are weakly nucleophilic bases, such as alkali metal hydroxides, for example sodium hydroxide.

The starting materials of the formula V in which $X_2$ is a radical of the formula $R_4''$—S— can be prepared, for example, by reacting a compound of the formula

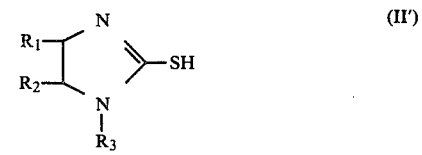

(II')

or preferably an alkali metal salt, such as the sodium salt, thereof, with a compound of the formula $R_4''$—Hal, in which Hal is halogen, such as chlorine, bromine or iodine, and, if desired, introducing a substituent into the 1-position of a resulting compound of the formula IV in which $R_3$ is hydrogen, by reaction with a lower alkyl halide of the formula $R_3$—Hal.

Starting materials of the formula V in which $X_2$ is a radical $R_R''-S-$ and $R_4''$ is a radical containing a sulfonium or ammonium group can advantageously be obtained from corresponding halogen compounds, for example those obtainable as described above, either by reacting these compounds with a disubstituted or trisubstituted amine, advantageously in the presence of a basic condensing agent, for example triethylamine, and, if desired, subsequently quaternising a trisubstituted amino group or converting it to a di-lower alkylamine oxide grouping, for example by means of m-chloroperbenzoic acid, or by reacting the said compounds with a lower alkyl mercaptide or substituted or unsubstituted phenyl mercaptide or di-lower alkyl sulfide and, if desired, lower alkylating lower alkylthio or oxidising lower alkylthio or substituted or unsubstituted phenylthio to corresponding sulfinyl or sulfonyl, for example by means of m-chloroperbenzoic acid. A compound of the formula IV which contains a substituted or unsubstituted hydrazono group in the radical $R_4''$ can also advantageously be prepared analogously by reacting a corresponding oxo compound of the formula IV with substituted or unsubstituted hydrazine.

Compounds of the formula I which are obtainable according to the invention can be converted to other compounds of the formula I in a conventional manner.

Thus, for example, nitro groups in the radicals $R_1$ and $R_2$ and also in aromatic groups as a constituent of $R_4$ can be reduced to amino in a conventional manner, such as with nascent hydrogen, for example with iron/hydrochloric acid.

Amino groups can also be substituted in a conventional manner, for example alkylated by reaction with an alkylating agent, such as one of those mentioned, in the presence of a basic condensing agent.

Furthermore, amino groups can be replaced by halogen by treatment with nitric acid and a hydrogen halide acid, such as hydrochloric acid, hydrobromic acid or hydriodic acid, if necessary in the presence of copper or a copper-I compound. Analogously, amino can be converted to hydroxyl or lower alkoxy by reaction with nitrous acid and warming the diazonium salt, thus obtainable, with water or with a lower alkanol. Furthermore, hydroxyl can be substituted in a conventional manner to give lower alkoxy, for example by reaction with a lower alkylating agent, for example a lower alkyl halide or di-lower alkyl sulfate, if necessary in the presence of potassium carbonate and advantageously in a ketone, such as acetone, or a higher-boiling alcohol, such as amyl alcohol. Conversely, lower alkoxy can be converted to hydroxyl by a conventional acid treatment, for example by the action of hydriodic acid or hydrogen bromide in acetic acid.

Furthermore, in compounds of the formula I in which $R_3$ is hydrogen, lower alkyl can be introduced in the 1-position, for example by a conventional reaction with a lower alkylating agent, such as a reactive ester of a lower alkanol, for example a lower alkyl halide, for example a lower alkyl chloride, lower alkyl bromide or lower alkyl iodide, advantageously in the presence of a basic condensing agent, such as an alkali metal hydroxide, alcoholate or amide, for example sodium hydroxide or potassium hydroxide, a sodium lower alkanolate, such sodium methanolate, sodium amide or lithium diisopropylamide. However, the N-lower alkylation can also be effected by reaction with an oxo-lower alkane, such as a lower alkanal or di-lower alkyl ketone in the presence of a reducing agent. Suitable reducing agents are, in particular, di-(light metal) hydrides, such as sodium borohydride or sodium cyanoborohydride, and also formaldehyde or formic acid and its salts.

Furthermore, in compounds of the formula I radicals $R_4$ can be converted into other radicals $R_4$.

For example, in the aliphatic moiety, resulting triple bonds can be reduced to double bonds and/or double bonds can be reduced to single bonds, for example by the action of hydrogen in the presence of a hydrogenation catalyst, such as a transition metal, for example Raney nickel, palladium- or platinum-on-charcoal, platinum oxide, triphenylphosphine-rhodium chloride or, for the reduction of triple bonds to double bonds, platinum-on-silica gel, advantageously in an inert solvent, for example ethanol, acetone or acetic acid, if necessary under elevated pressure and/or at elevated temperature. Unsaturated radicals $R_4$ can, however, also be converted to substituted saturated radicals $R_4$ by adding on water, hydrogen halide or halogen. Thus, substituted radicals $R_4$ which are saturated in the aliphatic moiety and contain hydroxyl or oxo can be obtained by adding on water in a conventional manner to double bonds or triple bonds, substituted radicals $R_4$ which are saturated in the aliphatic moiety and contain halogen or geminal dihalogen can be obtained by adding on hydrogen halide in a conventional manner to double bonds or triple bonds and substituted radicals $R_4$ which are saturated in the aliphatic moiety and contain vicinal dihalogen or vicinalgeminal tetrahalogen can be obtained by adding on halogen in a conventional manner to double bonds or triple bonds.

Furthermore, oxo in radicals $R_4$ containing oxo can be replaced by hydrogen by reduction, for example by the action of nascent hydrogen, produced, for example, by treating base metals with proton donors, for example by the treatment of zinc with hydrochloric acid or acetic acid, of aluminum, in the form of an amalgam, or sodium amalgam with water or of sodium with an alcohol, such as methanol. The replacement of oxo by hydrogen by reduction can also be effected by reaction with hydrazine in the presence of a metal base, for example of sodium hydroxide or potassium hydroxide or of an alkali metal alcoholate, such as sodium methanolate, in a high-boiling alcohol, such as ethylene glycol, diethylene glycol or diethylene glycol monomethyl ether, preferably at elevated temperature, for example at about 150° to 250° C. Oxo can also be reduced to hydroxyl in a conventional manner, for example by reaction with a light metal hydride, such as borane-tetrahydrofuran or diborane, or a di-(light metal) hydride, such as sodium borohydride, sodium cyanoborohydride or lithium aluminium hydride, or by reaction with a secondary alcohol, such as isopropanol or cyclohexanol, in the presence of an aluminium alcoholate. The reduction of oxo to hydroxyl can, however, also be effected with simultaneous introduction of a hydrocarbon radical on the carbonyl carbon atom, by reaction with an aliphatyl- or substituted or unsubstituted phenylaliphatyl-, heteroaryl- or phenyl-metal compound, for example substituted or unsubstituted phenyllithium or phenylmagnesium halide or, in particular, a lower alkyl-lithium or lower alkyl-magnesium halide. In an analogous manner a radical containing oxo in the β-position can be introduced by an aldol addition of a ketone or aldehyde onto an aldehydic oxo group, with reduction of the latter to hydroxyl. Oxo can also be replaced by geminal dihalogen by treatment with a suitable halogenating agent, such as phosphorus pentachloride or a di-lower alkylaminosulfur trifluoride, which is easily accessible by reaction of a di-lower alkyl-trimethylsilyl-amine with sulfur tetrafluoride in diethyl ether. Oxo can also be replaced by a divalent hydrocarbon radical, such as lower alkylidene, by reaction with a phosphorylide, for example with a triphenyl-lower alkylidenephosphorane. In an analogous manner, oxo can be replaced by formyl and hydrogen by reaction with a triphenyl-lower alkoxymethylene-phosphorane and hydrolysis of the enol-ether formed as an intermediate.

Furthermore, in radicals $R_4$ which contain hydroxyl the hydroxyl group can be replaced by hydrogen by reduction, for example as indicated above for the replacement of oxo by reduction by the action of hydrogen. Hydroxyl can also be oxidised to oxo by reaction with an oxidising heavy metal compound, for example with silver acetate or bismuth oxide, with dimethylsulfoxide in the presence of a trifluoromethanesulfonic acid anhydride or N-chlorosuccinimide, or with a ketone, such as acetone or cyclohexanone, in the presence of an aluminum alcoholate, such as aluminium ispropylate. Furthermore, hydroxyl can be converted to halogen by reaction with conventional halogenating agents, such as thionyl chloride or a di-lower alkylamino-sulfur trifluoride. A radical containing hydroxyl can also be converted to the corresponding radical $R_4$ which is unsaturated in the aliphatic moiety by conventional, for example acid-catalysed, elimination of water.

Furthermore, in radicals $R_4$ halogen can be converted to hydroxyl by conventional hydrolysis, for example hydrolysis catalysed by a weakly nucleophilic metal base, such as sodium hydroxide solution. Analogously, geminal dihalogen compounds can be hydrolysed to the corresponding oxo compounds. Halogen can also be replaced by hydrogen by reduction, by reaction with suitable light metal hydrides or di-(light metal) hydrides, for example with a tri-lower alkyl-aluminium hydride or with lithium aluminium hydride in the presence of aluminium trichloride, or can be replaced by a hydrocarbon radical by reduction, by reaction with a metal-organic compound, such as a lower alkyl-lithium or lower alkyl-magnesium halide. Radicals $R_4$ containing halogen can, however, also be converted to corresponding unsaturated radicals $R_4$ by the elimination of hydrogen halide.

Mixtures of stereoisomers obtainable according to the invention can be separated into the components in a conventional manner.

Thus, mixtures of diastereomers can be separated into the components on the basis of the differences in the physical properties of the components, by conventional physical methods of separation, such as crystallisation, chromatography, distillation or phase partition methods.

Mixtures of enantiomers, such as racemates, can be split into the enantiomers by converting the said mixtures into mixtures of diastereomers by crystallisation from optically active solvents, chromatography on optically active solids, the action of microorganisms or reaction with an optically active assistant, for example by converting them to mixtures of diastereomeric acid addition salts using an optically active acid, and by separating these mixtures of diastereomers into the diastereomers, from which the enantiomers can be liberated in the manner customary in the particular case. Optically active acids customarily used for this purpose are, for example, D- or L-tartaric acid, di-o-toluyltartaric acid, malic acid, mandelic acid, camphorsulfonic acids or quinic acid.

Furthermore, resulting free compounds can be converted to acid addition salts in a manner known per se, for example by reacting a solution of the free compound in a suitable solvent or solvent mixture with one of the abovementioned acids or with a solution thereof or with a suitable anion exchanger.

Resulting acid addition salts can be converted to the free compounds in a manner known per se, for example by treatment with a base, such as an alkali metal hydroxide, a metal carbonate or metal bicarbonate or ammonia, or with a suitable anion exchanger.

Resulting acid addition salts can be converted to other acid addition salts in a manner known per se, for example by treating a salt of an inorganic acid with a suitable metal salt, such as a sodium, barium or silver salt, of an acid in a suitable solvent, in which an inorganic salt which forms is insoluble and thus precipitates out of the reaction mixture.

The compounds, including their salts, can also be obtained in the form of the hydrates or can incorporate the solvent used for crystallisation.

Because of the close relationship between the novel compounds in the free form and in the form of their salts, what is stated in this specification in respect of the free compounds or the salts thereof also applies by analogy to the corresponding salts and free compounds.

The invention also relates to those embodiments of the process in which a compound obtainable as an intermediate at any process stage is used as the starting material and the missing process steps are carried out, or in which a starting material is formed under the reaction conditions or is used in the form of a derivative thereof, if desired in the form of a salt.

The starting materials used in the process of the present invention are preferably those which result in the compounds described initially as being particularly valuable. Novel starting materials and processes for their preparation are likewise a subject of the present invention.

The pharmaceutical preparations according to the invention, which contain compounds of the formula I or pharmaceutically usable salts thereof, are those which are intended for enteral, such as oral or rectal, and parenteral administration and for topical application to warm-blooded animals and which contain the pharmacological active ingredient on its own or together with a pharmaceutically usable carrier. The dosage of the active ingredient depends on the species of warm-blooded animal, the age and the individual condition and on the mode of administration. In the normal case an approximate daily dose of about 30–300 mg, advantageously divided into several equal partial doses, is to be proposed for a warm-blooded animal weighing about 75 kg, in the case of oral administration.

The novel pharmaceutical preparations contain, for example, from about 10% to about 80% and preferably from about 20% to about 60% of the active ingredient. Pharmaceutical preparations according to the invention for enteral or parenteral administration are, for example, those in dosage unit forms, such as sugar-coated tablets, tablets, capsules or suppositories, and also ampoules. These are prepared in a manner known per se, for example by means of conventional mixing, granulating, sugar-coating, dissolving or lyophilising methods. Thus, pharmaceutical preparations for oral use can be obtained by combining the active ingredient with solid carriers, granulating a resulting mixture if desired and processing the mixture or granules, after the addition of suitable assistants if desired or necessary, to tablets or sugar-coated tablet cores.

Suitable carriers are in particular fillers, such as sugars, for example lactose, sucrose, mannitol or sorbitol, cellulose preparations and/or calcium phosphates, for example tricalcium phosphate or calcium hydrogen phosphate, and also binders, such as starch pastes using, for example, maize starch, corn starch, rice starch or potato starch, gelatin, tragacanth, methylcellulose and/or polyvinylpyrrolidone, and/or, if desired, disintegrators, such as the above starches, and also carboxymethyl starch, crosslinked polyvinylpyrrolidone, agar or alginic acid or a salt thereof, such as sodium alginate. Adjuncts are in particular glidants and lubricants, for example silica, talc, stearic acid or salts thereof, such as magnesium stearate or calcium stearate, and/or polyethylene glycol. Sugar-coated tablet cores are provided with suitable coatings which can be resistant to gastric juices, using, inter alia, concentrated sugar solutions which may contain gum arabic, talc, polyvinylpyrrolidone, polyethylene glycol and/or titanium dioxide, shellack solutions in suitable organic solvents or solvent mixtures or, for the preparation of coatings resistant to gastric juices, solutions of suitable cellulose preparations, such as acetylcellulose phthalate or hydroxypropylmethylcellulose phthalate. Dyes or pigments can be added to the tablets or sugar-coated tablet coatings, for example to identify or indicate different doses of active ingredient.

Further pharmaceutical preparations for oral administration are dry-filled capsules made of gelatin, and also soft, sealed capsules made of gelatin and a plasticiser, such as glycerin or sorbitol. The dry-filled capsules can contain the active ingredient in the form of granules, for example in admixture with fillers, such as lactose, binders, such as starches, and/or lubricants, such as talc or magnesium stearate, and, if desired, stabilisers. In soft capsules, the active ingredient is preferably dissolved or suspended in suitable liquids, such as fatty oils, paraffin oil or liquid polyethylene glycols, to which stabilisers can also be added.

Suitable pharmaceutical preparations for rectal use are, for example, suppositories, which consist of a combination of the active ingredient with a suppository base. Examples of suitable suppository bases are natural or synthetic triglycerides, paraffin hydrocarbons, polyethylene glycols or higher alkanols. Gelatin rectal capsules, which contain a combination of the active ingredient with a base material, can also be used; examples of suitable base materials are liquid triglycerides, polyethylene glycols or paraffin hydrocarbons.

Preparations suitable for parenteral administration are, in particular, aqueous solutions of an active ingredient in a water-soluble form, for example in the form of a water-soluble salt, and also suspensions of the active ingredient, such as corresponding oily injection suspensions, for which suitable lipophilic solvents or vehicles, such as fatty oils, for example sesame oil, or synthetic fatty acid esters, for example ethyl oleate or triglycerides, are used, or aqueous injection suspensions, which contain substances which raise the viscosity, for example sodium carboxymethylcellulose, sorbitol and/or dextran, and can also contain stabilisers.

Suitable pharmaceutical preparations for topical application are, in particular, creams, ointments, pastes, foams, tinctures and solutions which contain from about 0.5 to about 20% of the active ingredient.

Creams are oil-in-water emulsions which contain more than 50% of water. Substances used as the oleaginous base are in particular fatty alcohols, for example lauryl alcohol, cetyl alcohol or stearyl alcohol, fatty acids, for example palmitic acid or stearic acid, liquid to solid waxes, for example isopropyl myristate, wool wax or beeswax, and/or hydrocarbons, for example petroleum jelly (petrolatum) or paraffin oil. Suitable emulsifiers are surface-active substances with predominantly hydrophilic properties, such as corresponding nonionic emulsifiers, for example fatty acid esters of polyalcohols or ethylene oxide adducts thereof, such as polyglycerol fatty acid esters or polyoxyethylene sorbitan fatty acid esters (Tweens), and also polyoxyethylene fatty alcohol ethers or polyoxyethylene fatty acid esters, or corresponding ionic emulsifiers, such as alkali metal salts of fatty alcohol sulfates, for example sodium lauryl-surface, sodium cetyl-sulfate or sodium stearyl-sulfate, which are customarily used in the presence of fatty alcohols, for example cetyl alcohol or stearyl alcohol. Additives to the aqueous phase are, inter alia, agents which reduce water loss from the creams by evaporation, for example polyalcohols, such as glycerol, sorbitol, propylene glycol and/or polyethylene glycols, and also preservatives, perfumes and the like.

Ointments are water-in-oil emulsions which contain up to 70% but preferably from about 20% to about 50% of water or aqueous phases. Substances used as the oleaginous phase are in particular hydrocarbons, for example petroleum jelly, paraffin oil and/or hard paraffins, which preferably contain hydroxy compounds suitable for improving the water-absorption, such as fatty alcohols or esters thereof, for example cetyl alcohol or wool wax alcohols, or wool wax. Emulsifiers are corresponding lipophilic substances, such as sorbitan fatty acid esters (Spans), for example sorbitan oleate and/or sorbitan isostearate. Additives to the aqueous phase are, inter alia, humectants, such as polyalcohols, for example glycerol, propylene glycol, sorbitol and/or polyethylene glycol, and preservatives, perfumes and the like.

Greasy ointments are anhydrous and, as the base, contain in particular hydrocarbons, for example paraffin, petroleum jelly and/or liquid paraffins, and also natural or partially synthetic fats, for example coconut fatty acid triglycerides, or preferably hardened oils, for example hydrogenated groundnut or castor oil, and also fatty acid partial esters of glycerol, for example glycerol monostearate and glycerol distearate, and, for example, the fatty alcohols which increase the water-absorption and emulsifiers and/or additives mentioned in connection with the ointments.

Pastes are creams and ointments containing powdered ingredients which absorb secretions, such as metal oxides, for example titanium oxide or zinc oxide, and talc and/or aluminum silicates, the purpose of which is to bind any moisture or secretion present.

Foams are administered from pressurised dispensers and are liquid oil-in-water emulsions in aerosol form, with halogenated hydrocarbons, such as chlorofluorolower alkanes, for example dichlorodifluoromethane and dichlorotetrafluoroethane, being used as propellants. Substances used as the oleaginous phase are, inter alia, hydrocarbons, for example paraffin oil, fatty alcohols, for example cetyl alcohol, fatty acid esters, for example isopropyl myristate, and/or other waxes. Emulsifiers used are, inter alia, mixtures of those emulsifiers which have predominantly hydrophilic properties, such as polyoxyethylene sorbitan fatty acid esters (Tweens), and those which have predominantly lipophilic properties, such as sorbitan fatty acid esters (Spans). In addition, the conventional additives are used, such as preservatives and the like.

Tinctures and solutions generally have an aqueous-ethanolic base to which there are added, inter alia, polyalcohols, for example glycerol, glycols and/or polyethylene glycol, as humectants for reducing water loss by evaporation, and fat-restoring substances, such as fatty acid esters with lower polyethylene glycols, i.e. lipophilic substances which are soluble in the aqueous mixture, as a replacement for fatty substances which are taken from the skin by the ethanol, and, if necessary, other assistants and additives.

The pharmaceutical preparations for topical use are prepared in a manner known per se, for example by dissolving or suspending the active ingredient in the base or in a part thereof, if necessary. When processing the active ingredient in the form of a solution, the ingredient is usually dissolved in one of the two phases before emulsification; when processing the active ingredient as a suspension, the ingredient is mixed with a part of the base after emulsification and the mixture is then added to the remainder of the formulation.

The present invention also relates to the use of the compounds of the formula I and the salts of such compounds having salt-forming properties, preferably for the treatment of inflammations, in particular of inflammatory chronic diseases of the rheumatic type, especially chronic arthritis.

The following examples illustrate the present invention without in any way restricting the scope thereof. Temperatures are in degrees Centigrade.

EXAMPLE 1

1.8 g of trans-4,5-diphenyl-imidazolidine-2-thione are dissolved in 20 ml of methanol, a solution of 0.3 g of sodium hydroxide in 2 ml of water and also 1.2 g of methyl iodide are added and the mixture is stirred at room temperature for 4 hours and left to stand overnight at 0°. The reaction mixture is evaporated to dryness, the residue is shaken with a mixture of 40 ml of water and 40 ml of ethyl acetate, the organic phase is separated off and the aqueous phase is washed with ethyl acetate. The organic phases are dried over sodium sulfate and evaporated to dryness. The crystalline residue is recrystallised, first from methanol and then from a mixture of diethyl ether and petroleum ether. Trans-2-methylthio-4,5-diphenyl-imidazoline with a melting point of 135°–137° is obtained.

The starting material can be prepared, for example, as follows:

11.5 g of D,L-1,2-diphenylethylenediamine (melting point 70°–71°), which is obtainable by reduction of benzil dioxime with sodium in ethanol, are dissolved in 230 ml of carbon disulfide. The solution is stirred for 3 hours and evaporated to dryness. The residue is taken up in a mixture of 40 ml of ethanol and 40 ml of water, 0.6 ml of concentrated hydrochloric acid is added and the mixture is refluxed for 48 hours. It is then evaporated to dryness and the residue is recrystallised from a mixture of ethanol and acetone. Trans-4,5-Diphenylimidazolidine-2-thione with a melting point of 223°–225° is obtained.

EXAMPLE 2

10.5 g of cis-4,5-diphenyl-imidazolidine-2-thione are dissolved in 120 ml of dimethylformamide. 1.9 g of sodium hydroxide in 12 ml of water are added, the mixture is diluted with 200 ml of dimethylformamide and 7 g of methyl iodide are added. The mixture is stirred for 4 hours at room temperature, allowed to stand overnight at 0° and evaporated to dryness and the residue is shaken thoroughly with a mixture of 200 ml of water and 200 ml of ethyl acetate. The crystals which remain are filtered off and boiled with methanol. By concentrating the methanolic solution, cis-2-methylthio-4,5-diphenyl-imidazoline hydroiodide with a melting point of 232°–245° (decomposition) is obtained. This product can be converted to cis-2-methylthio-4,5-diphenylimidazoline with a melting point of 132°–135° by dissolving in 60 ml of methanol, adding 30 ml of 2 N sodium hydroxide solution, concentrating and filtering off the product.

The ethyl acetate solution obtained above is separated off from the aqueous phase, dried over sodium sulfate and evaporated. The residual oil is boiled up with methanol, insoluble material is filtered off and the filtrate is evaporated. cis-1-Methyl-2-methylthio-4,5-diphenyl-imidazoline with a melting point of 148° (decomposition) is obtained.

The cis-4,5-diphenyl-imidazolidine-2-thione which is used as the starting material can be prepared in a manner analogous to that described in Example 1, using meso-1,2-diphenylethylenediamine as the starting material. It melts at 252°. The meso-diphenylethylenediamine can be obtained by hydrogenation of benzil dioxime in a mixture of ethanol and N sodium hydroxide solution in the presence of palladium (5% on charcoal) under normal pressure and at room temperature.

EXAMPLE 3

The following compounds are also obtained in a manner analogous to that described in Examples 1 and 2: cis-2-ethylthio-4,5-diphenyl-imidazoline, m.p. 94°–6°, trans-2-ethylthio-4,5-diphenyl-imidazoline, m.p. 130°–2°, cis-4,5-bis-(p-methoxyphenyl)-2-methylthio-imidazoline, m.p. 163°–4°, trans-4,5-bis-(p-methoxyphenyl)-2-methylthio-imidazoline, cis-2-ethylthio-4,5-bis-(p-chlorophenyl)-imidazoline hydrochloride, m.p. 226°–7°, trans-2-ethylthio-4,5-bis-(p-chlorophenyl)-imidazoline, cis-4,5-bis(p-chlorophenyl)-2-methylthio-imidazoline hydrochloride, m.p. 224° decomp., trans-4,5-bis-(p-chlorophenyl)-2-methylthio-imidazoline, cis-2-ethylthio-4,5-bis-(p-methoxyphenyl)-imidazoline, m.p. 92°–3°, trans-2-ethylthio-4,5-bis-(p-methoxyphenyl)-imidazoline, and trans-2-propylthio-4,5-diphenyl-imidazoline, m.p. 133°–35°.

EXAMPLE 4

2.5 g of D,L-trans-4,5-diphenyl-imidazolidine-2-thione are dissolved in 25 ml of methanol, 1.7 g of methyl iodide are added and the mixture is refluxed for 15 hours. A further 0.4 g of methyl iodide is then added and the mixture is refluxed for a further 5 hours. It is then evaporated to dryness and the residue is suspended in concentrated, aqueous ammonia solution. The D,L-trans-2-methylthio-4,5-diphenyl-imidazoline which has precipitated or remained undissolved is filtered off and recrystallised from ethanol. It melts at 135°–137°.

The starting material can be prepared in a manner analogous to that described in Example 1. However, the D,L-1,2-diphenylethylenediamine is more advantageously prepared by acetylation of 2,4,5-triphenyl-4,5-dihydroimidazole by means of acetic anhydride and sodium acetate and subsequent treatment of the product with hydrochloric acid. The D,L-1,2-diphenylethylenediamine bis-hydrochloride obtainable by this method as the first product melts at 247°–249° and the D,L-trans-4,5-diphenylimidazolidine-2-thione obtainable by reacting the base with carbon disulfide melts at 221°–223°.

D-trans-2-Methylthio-4,5-diphenyl-imidazoline and L-trans-2-methylthio-4,5-diphenyl-imidazoline can be prepared in an analogous manner, using 2,4,5-triphenyl-4,5-dihydro-imidazole as the starting material, via D,L-1,2-diphenylethylenediamine, splitting off the latter in the manner known from the literature into D-1,2-diphenylethylenediamine and L-1,2-diphenylethylenediamine and reacting these products first with carbon disulfide and then with methyl iodide.

EXAMPLE 5

17.5 g of cis-4,5-diphenyl-imidazolidine-2-thione are dissolved in 200 ml of dimethylformamide and first a solution of 3.2 g of sodium hydroxide in 20 ml of water and then 11.6 g of methyl iodide are added. The mixture is stirred for 6.5 hours at room temperature and evaporated to dryness, the residue is stirred with 350 ml of water and, after leaving to stand for some time, the mixture is filtered with suction, the solid material from the mixture is dissolved, whilst still moist, in 350 ml of ethanol and 50 ml of 2 N sodium hydroxide solution and 170 ml of water are added. The crystalline precipitate is filtered off with suction, filtered through silica gel using chloroform as the eluant and recrystallised from isopropanol/petroleum ether. cis-2-Methylthio-4,5-diphenyl-imidazoline with a melting point of 132°–134° is obtained.

EXAMPLE 6

9.4 g of cis-4,5-diphenyl-imidazolidine-2-thione are dissolved in 150 ml of dimethylformamide and first 15 ml of 2 N sodium hydroxide solution and then 1.86 mg of methyl iodide in 10 ml of dimethylformamide are added. The mixture is stirred for 12 hours at room temperature, a futther 10 ml of 2 N sodium hydroxide solution and 1.24 mg of methyl iodide, dissolved in 10 ml of dimethylformamide, are added and the mixture is stirred for a further 12 hours. It is then poured into water, the precipitate is filtered off and dissolved in 200 ml of chloroform and the solution is dried over sodium sulfate and concentrated until it becomes turbid. Crystallisation takes place after some time. The crystalline product is filtered off with suction, filtered through silica gel using chloroform as the eluant and recrystallised from isopropanol/petroleum ether. cis-2-Methylthio-4,5-bis-(p-methoxyphenyl)-imidazoline with a melting point of 132°–134° is obtained.

The starting material can be prepared, for example, as follows:

67.7 g of meso-1,2-bis-(p-methoxyphenyl)-ethylenediamine, which is obtainable by hydrogenation of p-anisoindioxine in the presence of palladium-on-charcoal and has a melting point of 151°–152.5°, are dissolved in 1,400 ml of ethanol, 27 ml of carbon disulfide are added and the mixture is refluxed for 16 hours, with stirring. The crystals which have precipitated out are filtered off with suction and suspended in 1,200 ml of ethanol and the suspension is refluxed until the evolution of hydrogen sulfide has ceased (about 30 hours). cis-4,5-Bis-(p-methoxyphenyl)-imidazolidine-2-thione with a melting point of 226°–227° is obtained.

EXAMPLE 7

12 g of cis-4,5-bis-(p-methoxyphenyl)-imidazolidine-2-thione are added to a solution of 0.88 g of sodium in 13 ml of methanol. The mixture is then diluted with 200 ml of dimethylformamide and left to stand overnight, 4 ml of ethyl iodide are added and the mixture is stirred for 5 hours at room temperature and poured into 300 ml of water. The crystals which have precipitated out are filtered off with suction and dissolved in methylene chloride. The solution is dried over sodium sulfate and evaporated and the residue is dissolved in acetone. The acetone solution is rendered weakly acid with methanolic hydrochloric acid (4.5μ) and the cis-2-ethylthio-4,5-bis-(p-methoxyphenyl)-imidazoline hydrochloride which has precipitated is filtered off. In order to liberate the base, this hydrochloride is treated with 2 N sodium hydroxide solution and the crude base is then rcrystallised from isopropanol/petroleum ether. cis-2-Ethylthio-4,5-bis-(p-methoxyphenyl)-imidazoline with a melting point of 92°–93° is obtained.

EXAMPLE 8

10.3 g of cis-4,5-diphenyl-imidazolidine-2-thione are suspended in a mixture of 25 ml of methanol and 3.8 ml of ethyl iodide and the suspension is refluxed for 1 hour, with stirring. A further 75 ml of methanol are then added and the mixture is refluxed for 16 hours. The clear reaction solution is evaporated to dryness and the residue is taken up in a mixture of 150 ml of water and 250 ml of ethyl acetate. In order to liberate the base, the mixture is rendered alkaline iwth concentrated aqueous ammonia solution and shaken thoroughly and the organic phase is separated off, dried over sodium sulfate and evaporated. Recrystallisation of the residue from isopropanol/petroleum ether yields cis-2-ethylthio-4,5-diphenyl-imidazoline with a melting point of 95°–96°.

cis-4,5-Diphenyl-2-propylthio-imidazoline can be obtained analogously, by reaction with propyl iodide.

EXAMPLE 9

5 g of cis-bis-(p-chlorophenyl)-imidazolidine-2-thione are dissolved in 100 ml of dimethylformamide, first 0.7 g of sodium hydroxide in 4.4 ml of water and then 1.3 g of methyl iodide are added and the mixture is left to stand overnight. It is then poured into water and extracted several times with ethyl acetate. The extracts are combined, dried over sodium sulfate and evaporated. The residual oil is purified by chromatography through a silica gel column using chloroform as the solvent. This yields cis-2-methylthio-4,5-bis-(p-chlorophenyl)-imidazoline, which for characterisation can be converted by treatment with ethanolic hydrochloric acid to cis-2-methylthio-4,5-bis(p-chlorophenyl)-imidazoline hydrochloride with a melting point of 224°.

The starting material can be prepared, for example, as follows:

22.8 g of meso-1,2-bis-(p-chlorophenyl)-ethylenediamine, which is accessible in a known manner from p-chlorobenzaldehyde by reaction with ammonium acetate and subsequent treatment of the product with dilute sulfuric acid and has a melting point of 136°–138°, are dissolved in 350 ml of ethanol, 8.7 ml of carbon disulfide are added and the mixture is refluxed for 12 hours. The solution is concentrated and after crystallisation has taken place cis-4,5-bis-(p-chlorophenyl)-imidazolidine-2-thione is filtered off with suction. When recrystallised from methanol, it melts at 197°–208°.

EXAMPLE 10

20 ml of methanol and 0.9 g of ethyl iodide are added to 2.2 g of cis-4,5-bis-(p-chlorophenyl)-imidazolidine-2-thione and the mixture is refluxed for 22 hours. The mixture is allowed to cool, the colourless crystals are filtered off with suction and taken up in 100 ml of water and 100 ml of ethyl acetate, concentrated aqueous ammonia solution is added until an alkaline reaction is obtained, the organic phase is separated off, dried over sodium sulfate and evaporated to dryness and the residue is subjected to chromatography on silica gel using methylene chloride as the solvent. After evaporating, cis-2-ethylthio-4,5-bis-(p-chlorophenyl)-imidazole is obtained in the form of an oil and, for characterisation, this can be converted, in isopropanol as the solvent, by treatment with a solution of hydrogen chloride in ethyl acetate into 2-ethylthio-4,5-bis-(p-chlorophenyl)-imidazoline hydrochloride with a melting point of 226°–227°.

EXAMPLE 11

25 ml of methanol and 1.85 g of ethyl iodide are added to 2.5 g of DL-trans-4,5-diphenyl-imidazolidine-2-thione and the mixture is refluxed for 15 hours. A further 0.4 g of ethyl iodide is then added and the mixture is refluxed for a further 5 hours. It is then evaporated to dryness. DL-trans-2-Ethylthio-4,5-diphenyl-imidazoline hydroiodide is obtained. In order to convert it to the base, this hydroiodide is suspended in 100 ml of ethyl acetate and 100 ml of water, the suspension is rendered alkaline with concentrated aqueous ammonia solution and the organic phase is separated off, dried over sodium sulfate and evaporated. DL-trans-2-Ethylthio-4,5-diphenyl-imidazoline with a melting point of 130°–132° is obtained.

D-trans-2-Ethylthio-4,5-diphenyl-imidazoline, L-trans-2-ethylthio-4,5-diphenyl-imidazoline and D,L-trans-2-propylthio-4,5-diphenyl-imidazoline, with a melting point of 134°–135°, can be prepared analogously, using D- and/or L-trans-4,5-diphenyl-imidazlidine-2-thione as the starting material.

EXAMPLE 12

4.3 g of cis-2-(2-acetoxyethyl)-4,5-bis-(p-methoxyphenyl)-imidazoline are refluxed with 100 ml of methanol and 25 ml of 2 N sodium hydroxide solution for 4 hours. The mixture is filtered hot to remove the insoluble matter, the filtrate is evaporated to dryness and the residue is recrystallised from isopropanol/petroleum ether. cis-2-(2-Hydroxyethyl)-4,5-bis-(p-methoxyphenyl)-imidazole is obtained in the form of an oil.

The starting material can be prepared, for example, as follows:

8 g of cis-4,5-bis-(p-methoxyphenyl)-imidazolidine-2-thione are refluxed in 50 ml of methanol with 3.5 g of 2-acetoxyethyl chloride for 22 hours. The mixture is evaporated to dryness, the residue is taken up 100 ml of ethyl acetate and 25 ml of water, concentrated aqueous ammonia solution is added until an alkaline reaction is obtained and the organic phase is separated off, dried over sodium sulfate and evaporated to dryness. This yields cis-2-(2-actoxyethyl)-4,5-bis-(p-methoxyphenyl)-imidazoline which can be used without further purification.

EXAMPLE 13

7.5 g of cis-1-methyl-4-phenyl-5-(3-pyridyl)-imidazolidine-2-thione are refluxed in 100 ml of methanol with 5.5 g of ethyl iodide for 22 hours. The mixture is evaporated to dryness, the residue is taken up in 100 ml of ethyl acetate and 25 ml of water, concentrated aqueous ammonia solution is added until an alkaline reaction is obtained and the organic phase is separated off, dried over sodium sulfate and evaporated to dryness. This yields cis-2-ethylthio-1-methyl-4-phenyl-5-(3-pyridyl)-imidazoline.

The starting material can be obtained as follows:

13.5 g of benzyl 3-pyridyl ketone are stirred together with 50 ml of pyridine and a solution of 10 g of hydroxylamine hydrochloride in 20 ml of pyridine for 6 hours at 100°. The reaction mixture is poured onto ice/water and the resulting mixture is stirred for a further 15 minutes. The crystals which have precipitated out are filtered off with suction, washed with water and dried under a high vacuum. Benzyl 3-pyridyl ketone-oxime with a melting point of 122°–126° is obtianed.

A solution of 5.8 g of p-toluenesulfonyl chloride in 15 ml of pyridine is added dropwise in the course of 5 minutes to a stirred solution, which is at −10°, of 6.4 g of benzyl 3-pyridyl ketone-oxime in 15 ml of pyridine. The reaction mixture is kept in a refrigerator for 24 hours and is then poured onto ice/water. After prolonged stirring and grinding, the oil which has precipitated out solidifies to crystals. These are filtered off with suction, washed with water and dried under a high vacuum. This yields 11.6 g of a crude product with a melting point of 87°–92°, which, however, according to thin layer chromatography still contains educt. The product is employed direct in the next stage.

8.7 g of the crude product (benzyl 3-pyridyl ketone-oxime-p-toluenesulfonate) are suspended in 70 ml of absolute ethanol and a solution of 2.8 g of potassium tert.-butylate in 25 ml of absolute ethanol is added dropwise at 0°, with stirring. The reaction mixture is stirred at 0° for 2 hours. The suspension is filtered with suction and the filtrate is immediately employed in the next stage.

2.4 g of methyl isothiocyanate are added to the solution, which contains α-amino-benzyl 3-pyridyl ketone, and the mixture is stirred for 3 hours at 0°–5°. 2.3 g of sodium borohydride are then added in portions and the mixture is stirred for 4 hours at 0°–10°. It is then decanted in order to remove excess sodium borohydride, 2 ml of acetone are added and the resulting mixture is refluxed for 18 hours. After cooling, 2.1 g of crude 1-methyl-4-p-phenyl-5-(3-pyridyl)-imidazolidine-2-thione can be filtered off from the reaction mixture with suction. The filtrate contains further amounts of the product.

EXAMPLE 14

Tablets containing 25 mg of active ingredient, for example cis-2-methylthio-4,5-diphenyl-imidazoline, can be prepared as follows:

| Constituents (for 1,000 tablets) | |
| --- | --- |
| active ingredient | 25.0 g |
| lactose | 100.7 g |
| corn starch | 7.5 g |
| polyethylene glycol 6000 | 5.0 g |
| talc | 5.0 g |
| magnesium stearate | 1.8 g |

-continued

| Constituents (for 1,000 tablets) | |
|---|---|
| demineralised water | q.s. |

Preparation

All of the solid ingredients are first forced through a sieve of 0.6 mm mesh width. The active ingredient, the lactose, the talc, the magnesium stearate and half of the starch are then mixed. The other half of the starch is suspended in 40 ml of water and this suspension is added to a boiling solution of the polyethylene glycol in 100 ml of water and, after adding the abovementioned mixture, the whole is granulated, with the additon of water if necessary. The granules are dried overnight at 35°, forced through a sieve of 1.2 mm mesh width and compressed to tablets which are concave on both sides and about 6 mm in diameter.

Tablets containing, in each case, 25 mg of one of the other compounds of the formula I and named in Examples 1 to 3 can also be prepared in an analogous manner.

EXAMPLE 15

Tablets containing 25 mg of a compound obtainable according to one of Examples 4 to 13 can also be prepared in a manner analogous to that described in Example 14.

We claim:

1. A compound of the formula

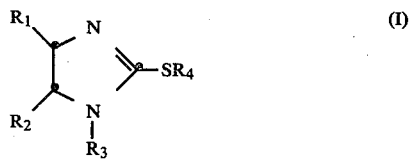

in which $R_1$ and $R_2$ independently of one another are unsubstituted phenyl, or phenyl substituted by lower alkyl, lower alkoxy, halogen with an atomic number of not more than 35, nitro, amino, or N,N-di-lower alkylamino, unsubstituted pyridyl, or pyridyl substituted by lower alkyl or lower alkoxy, and unsubstituted thienyl, $R_3$ is hydrogen or lower alkyl, and $R_4$ is lower alkyl, phenyl-lower alkyl, phenyl-lower alkyl substituted in the phenyl-part by lower alkyl, lower alkoxy, halogen with an atomic number of not more than 35, nitro, amino, or N,N-di-lower alkylamino, or denotes hydroxy-lower alkyl, lower alkoxy-lower alkyl, lower alkyl-thio-lower alkyl, phenoxy-lower alkyl, or phenylthio-lower alkyl, wherein hydroxy, lower alkoxy, lower alkylthio, phenoxy and phenylthio are substituted in higher than the α-position, or a pharmaceutically usable salt thereof.

2. A compound according to claim 1, in which $R_1$ and $R_2$ independently of one another are phenyl which is unsubstituted or substituted by lower alkyl having not more than 4 C atoms, lower alkoxy having not more than 4 C-atoms or halogen with an atomic number of not more than 35, or are unsubstituted pyridyl, $R_3$ is hydrogen and $R_4$ is lower alkyl having not more than 4 C atoms, or a pharmaceutically usable salt thereof.

3. A compound of claim 1 and being the D-trans-4,5-diphenyl-2-methylthio-imidazoline or a pharmaceutically usable salt thereof.

4. A compound of claim 1 and being the L-trans-4,5-diphenyl-2-methylthio-imidazoline or a pharmaceutically usable salt thereof.

5. A compound of claim 1 and being the cis-2-ethylthio-1-methyl-4-phenyl-5-(3-pyridyl)-imidazoline or a pharmaceutically usable salt thereof.

6. A compound of claim 1 and being the 2-Methylthio-4,5-diphenyl-imidazoline or a pharmaceutically useable salt thereof.

7. A compound of claim 1 and being the 2-Ethylthio-4,5-diphenyl-imidazoline or a pharmaceutically useable salt thereof.

8. A compound of claim 1 and being the 4,5-Bis-(p-methoxyphenyl)-2-methylthio-imidazoline or a pharmaceutically useable salt thereof.

9. A compound of claim 1 and being the 4,5-Bis-(p-methoxyphenyl)-2-ethylthio-imidazoline or a pharmaceutically useable salt thereof.

10. A compound of claim 1 and being the 2-Methylthio-4,5-bis-(p-chlorophenyl)-imidazoline or a pharmaceutically useable salt thereof.

11. A compound of claim 1 and being the 2-Ethylthio-4,5-bis-(p-chlorophenyl)-imidazoline or a pharmaceutically useable salt thereof.

12. A compound according to claim 1, in the cis form.

13. A compound according to claim 1, in the trans form.

14. An anti-inflammatory pharmaceutical composition comprising an anti-inflammatory effective amount of a compound according to claim 1 together with a conventional pharmaceutically usable carrier.

15. An anti-inflammatory pharmaceutical composition comprising an anti-inflammatory effective amount of a compound according to claim 3 or 4 together with a conventional pharmaceutically usable carrier.

* * * * *